US008569238B2

(12) United States Patent
Kamei et al.

(10) Patent No.: US 8,569,238 B2
(45) Date of Patent: Oct. 29, 2013

(54) PLASMA PROTEIN EFFECTIVE FOR SUPPRESSING COUGH

(71) Applicant: The Chemo-Sero-Therapeutic Research Institute, Kumamoto (JP)

(72) Inventors: Shintaro Kamei, Kumamoto (JP); Asami Shindome, Kumamoto (JP); Takayoshi Hamamoto, Kumamoto (JP); Hiroaki Maeda, Kikuchi (JP); Masaki Hirashima, Kikuchi (JP); Sachio Okuda, Kumamoto (JP); Misako Umehashi, Kumamoto (JP); Sachie Ogawa, Cambridge, MA (US); Megumi Imuta, Kawasaki (JP); Norio Akaike, Kumamoto (JP); Kazuo Takahama, Kumamoto (JP); Ryoko Wada, Kumamoto (JP)

(73) Assignees: The Chemo-Sero-Therapeutic Research Institute, Kumamoto-shi (JP); Ginkyo Academy Kumamoto Health Science University, Kumamoto-shi (JP); National University Corporation Kumamoto University, Kumamoto-shi (JP)

( * ) Notice: Subject to any disclaimer, the term of this patent is extended or adjusted under 35 U.S.C. 154(b) by 0 days.

(21) Appl. No.: 13/845,643

(22) Filed: Mar. 18, 2013

(65) Prior Publication Data

US 2013/0224179 A1 Aug. 29, 2013

Related U.S. Application Data

(63) Continuation of application No. 13/389,215, filed as application No. PCT/JP2010/063329 on Aug. 5, 2010.

(30) Foreign Application Priority Data

Aug. 6, 2009 (JP) ................. 2009-182945

(51) Int. Cl.
*A61K 38/00* (2006.01)
*C07K 1/00* (2006.01)
*C07K 14/00* (2006.01)
*C07K 16/00* (2006.01)
*C07K 17/00* (2006.01)

(52) U.S. Cl.
USPC ............................ 514/15.3; 514/1.1; 514/850

(58) Field of Classification Search
None
See application file for complete search history.

(56) References Cited

U.S. PATENT DOCUMENTS

| 5,792,623 A * | 8/1998 | Turecek | 435/68.1 |
| 2005/0070477 A1* | 3/2005 | Cochrane | 514/12 |
| 2005/0281781 A1* | 12/2005 | Ostroff | 424/93.2 |

FOREIGN PATENT DOCUMENTS

| JP | 2000-344682 | 12/2000 |
| JP | 2003-327529 | 11/2003 |
| JP | 2007-99728 | 4/2007 |

OTHER PUBLICATIONS

Chapter 84, Mechanisms of Cough, J. M. Madison and R. S. Irwin, in Asthma and Rhinitis, Second Edition, Apr. 16, 2008.*
Gailani, D. et al., "Structural and functional features of factor XI", Journal of Thrombosis and Haemostasis, vol. 7 Suppl 1, p. 75-8. (2009).
Undem, B.J. et al., "Physiology and plasticity of putative cough fibres in the Guinea pig", Pulmonary Pharmacology & Therapeutics, vol. 15, No. 3, p. 193-8. (2002).
Canning, B.J. et al., "Vagal afferent nerves regulating the cough reflex", Respiratory Physiology & Neurobiology, vol. 152, No. 3, p. 223-42. (2006).
Takahama, K. et al., "Differential effect of codeine on coughs caused by mechanical stimulation of two different sites in the airway of guinea pigs", European Journal of Pharmacology, vol. 329, No. 1, p. 93-7. (1997).
International Search Report issued on Aug. 31, 2010 in PCT/JP10/063329 filed on Aug. 5, 2010.
Bradley J. Undem, et al., "Physiology and Plasticity of Putative Cough Fibres in the Guinea Pig", Pulmonary Pharmacology & Therapeutics, vol. 15, No. 3, 2002, pp. 193-198 (submitting Statement of Relevancy only, reference previously filed Feb. 6, 2012).
Supplementary European Search Report dated Feb. 6, 2013 as received in the corresponding European Patent Application No. 10806533.5.
Kazuhiko Shinagawa, et al., "Coagulation factor Xa modulates airway remodeling in a murine model of asthma", American Journal of Respiratory and Critical Care Medicine, American Lung Association, vol. 175, No. 2, pp. 136-143, (2007).
Chapter 84, Mechanisms of Cough, J.M. Madison and R.S.. Irwin, in Asthma and Rhinitis, Second Edition, Apr. 16, 2008.

* cited by examiner

Primary Examiner — Maury Audet
Assistant Examiner — Joseph Fischer
(74) Attorney, Agent, or Firm — Oblon, Spivak, McClelland, Maier & Neustadt, L.L.P.

(57) ABSTRACT

The activated Factor XI is provided as an antitussive for cough caused by the stimulation at the tracheal bifurcation such as chronic cough. A pharmaceutical composition for prevention, treatment and/or symptom amelioration of cough, comprising a polypeptide chain as an active ingredient and a pharmaceutically acceptable carrier, wherein the polypeptide chain consists of a full length amino acid sequence constituting activated Factor XI (hereinafter also referred to as "FXIa"), the amino acid sequence with one or several amino acids therein being deleted, substituted or added, or a partial sequence of either of the above amino acid sequences, or an amino acid sequence comprising as a part any of the above amino acid sequences.

12 Claims, No Drawings

PLASMA PROTEIN EFFECTIVE FOR SUPPRESSING COUGH

This application is a division of U.S. Ser. No. 13/389,215, filed May 17, 2012, which is the U.S. national-stage of PCT/JP10/63329, filed Aug. 5, 2010.

TECHNICAL FIELD

The present invention relates to an antitussive pharmaceutical composition comprising activated Factor XI (hereinafter also referred to as "FXIa") as an active ingredient.

BACKGROUND ART

Cough is a biophylactic reaction induced by inhalation of foreign substances, accumulation of sputum in the respiratory tract, and the like. Cough also occurs upon various clinical conditions such as common cold and respiratory tract inflammation. Exhaustion accompanied by cough is intensive, especially in the case of the aged suffering from influenza, and may be a direct cause of death. Further, continuing cough may cause chest pain, urinary incontinence, shortage of sleep, exhaustion, and the like to thereby trouble daily life, and therefore results in QOL deterioration. Cough may be categorized as cough by chronic bronchitis, cough after acute upper respiratory inflammation, cough accompanied by oral administration of an angiotensin-converting enzyme inhibitor, cough by gastroesophageal reflux, cough by sinobronchial syndrome, cough by cough variant asthma, atopic cough, and the like. Cough not only has clinical diversity but also has not yet fully elucidated for its mechanism, and therefore an effective antitussive is considered to be in short supply.

The afferent nerve involved in sensation at the respiratory tract and an onset of cough may be classified broadly into medullated Aδ-fiber and nonmedullated C-fiber. Among them, Aδ-fiber plays an afferent role of a cough reflex and is mostly well distributed in the laryngeal trachea. At a terminal receptor of the Aδ nerve exist RARs (rapidly adapting receptor) that may sensitively react to a mechanical stimulation such as mucus and eventually cause a cough reflex via the cough center but may hardly be affected by an inflammation-related mediator such as bradykinin. On the other hand, C-fiber, occurring at a peripheral part of the lower respiratory tract, is highly sensitive to chemical substances but is not responsive to a mechanical stimulation (Non-patent Reference 1).

A medicament currently used as an antitussive may be broadly classified into a central antitussive and a peripheral antitussive. A central antitussive may suppress a cough reflex by blocking the cough center to thereby exert an antitussive efficacy. A central antitussive may further be classified into narcotic and normarcotic ones. A typical narcotic antitussive includes codeine and dihydrocodeine phosphate. A narcotic antitussive may exert a potent antitussive efficacy but has a problem that it has adverse side effects such as addiction, drowsiness, constipation, nausea, vomiting, headache, hallucination, and the like and may not be used for bronchial asthma accompanied by respiratory tract inflammation or obstructive pulmonary diseases due to induction of bronchial muscle contraction (Patent Reference 1 and Patent Reference 2). A typical normarcotic antitussive includes noscapine, alloclamide hydrochloride, and dextromethorphan hydrobromide. A normarcotic antitussive is said to be free from tolerance or dependence with weak adverse side effects but still affects on those other than the cough center, causing adverse side effects such as dizziness, drowsiness, headache, and the like. Further, its antitussive activity is weaker than that of a narcotic antitussive with almost no efficacy for psychogenic cough or pertussis.

On the other hand, a peripheral antitussive may be classified into a cough drop, a variety of Chinese herbal medicines, a mouthwash, an expectorant, and a bronchodilator. They affect on the laryngeal trachea or the tracheal bifurcation to suppress a cough reflex but, unlike a central antitussive, cannot fully suppress an onset of cough and their effects are relatively slight. Another peripheral antitussive includes a steroid (inhalation and oral agent) and an antihistamine with which some cough, with no amelioration of symptoms, may become chronic, for which any medicament may hardly be effective. Recently, it is suggested that C-fiber may be involved in intractable chronic cough. Therefore, at a clinical stage, an antitussive suppressing cough caused by stimulation at the laryngeal trachea and at the tracheal bifurcation is desired but currently available antitussives are not efficacious (Patent Reference 3).

FXI is a plasma protein which functions at a contact layer of blood coagulation cascade and exists as a homodimer of a molecular weight of approximately 160,000 which comprises single-strand glycoproteins of a molecular weight of approximately 80,000 bound with each other via a single S—S bond. Immature FXI immediately after production is added with a signal sequence, which is cleaved to produce mature FXI. The monomer consists of an N terminal H chain comprising four apple domains, each consisting of approximately 90 amino acid residues, and an L chain as a protease domain. FXI alone does not have a property of adhering to a surface of a foreign substance. After FXI binds to a surface of a foreign substance via a high molecular weight kininogen (HMW-K), it is subject to limited hydrolysis by activated Factor XII (hereinafter also referred to as "FXIIa"), and the like, to be activated to FXIa. For the function of FXIa, the activation of Factor IX (hereinafter also referred to as "FIX") in the presence of $Ca^{2+}$ and the activity to degrade FXII, HMW-K and plasminogen under specific in vitro conditions have hitherto been reported, but an antitussive efficacy has not.

Patent Reference 1: JP-A-2000-344682
Patent Reference 2: JP-A-2003-327529
Patent Reference 3: JP-A-2007-099728
Non-patent Reference 1: Physiology and Plasticity of Putative Cough Fibres in the Guinea Pig: Pulm. Pharmacol Ther.: Undem B J, et al., 2002: 15: p 193-198

DISCLOSURE OF THE INVENTION

Technical Problem to be Solved by the Invention

As described above, at a clinical stage, an antitussive suppressing both cough caused by stimulation at the laryngeal trachea and at the tracheal bifurcation is desired. Currently available antitussives are effective against cough caused by stimulation at the laryngeal trachea but could not fully relieve cough caused by stimulation at the tracheal bifurcation. The present invention provides a novel antitussive which can relieve both cough caused by stimulation at the laryngeal trachea and at the tracheal bifurcation.

Means for Solving the Problems

Human plasma contains a variety of physiologically active substances such as albumin, an immunoglobulin and fibrinogen but, it is thought, contains many functionally unknown substances, viewing that many of them exist in a trace amount. Therefore, the present inventors have focused on the fact that these physiologically active substances are concentrated in fractions adsorbed and eluted on heparin chromatography and, among the adsorbed fractions on heparin chromatography in a fractionation step of the human plasma in a production scale, collected discarded fractions, from which antithrombin is removed, and then divided into eight fractions by another development using heparin chromatography. Each of the fractions was assessed for their physiological activities from various aspects. As one of such assessments, the present inventors assessed their antitussive efficacy with a guinea pig cough model by Takahama et al., which allows for assessment of both a cough reflex caused by the laryngeal trachea stimulation (Aδ-fiber stimulative) and a cough reflex caused by the tracheal bifurcation stimulation (C-fiber stimulative) (Differential effect of codeine on coughs caused by a mechanical stimulation of two different sites in the airway of guinea pigs: Eur. J. Phamacol.: Takahama K. et al., 1997: 329: p 93-97).

As a result, surprisingly, the present inventors have found that a particular fraction showed an antitussive activity to both of a cough reflex caused by the tracheal bifurcation stimulation (Aδ-fiber stimulative) and a cough reflex caused by the laryngeal trachea stimulation (C-fiber stimulative). Thus, the present inventors developed the active fraction on rechromatography and size exclusion chromatography, and then, by two-dimensional electrophoresis and MALDI-TOF MS, identified active substances in the fraction. As a result, surprisingly, the present inventors have found that the active substance was activated Factor XI (FXIa), i.e. that FXIa had a potent antitussive activity for both a cough reflex caused by the laryngeal trachea stimulation (Aδ-fiber stimulative) and a cough reflex caused by the tracheal bifurcation stimulation (C-fiber stimulative) to thereby complete the present invention.

Accordingly, the present invention includes the followings:
[1] A pharmaceutical composition for prevention, treatment and/or symptom amelioration of cough, comprising a polypeptide chain as an active ingredient and a pharmaceutically acceptable carrier,
wherein the polypeptide chain consists of a full length amino acid sequence constituting activated Factor XI (hereinafter also referred to as "FXIa"), the amino acid sequence with one or several amino acids therein being deleted, substituted or added, or a partial sequence of either of the above amino acid sequences, or an amino acid sequence comprising as a part any of the above amino acid sequences.
[2] The pharmaceutical composition according to [1], wherein the cough is caused by stimulation at the tracheal bifurcation.

Effects of the Invention

According to the above report by Takahama et al., in the guinea pig cough model, codeine significantly suppresses a cough reflex caused by the laryngeal trachea stimulation at 10 mg/kg (oral), but does not show a significant suppression of the tracheal bifurcation stimulation until administration at 20-50 mg/kg is given. On the other hand, for FXIa in accordance with the present invention, an antitussive efficacy on both the laryngeal trachea stimulation and the tracheal bifurcation stimulation with administration of 29 μL/kg at 0.15-15 μg/mL (i.v.) was observed (the dose corresponds to approximately 4.4-435 ng/kg with a body weight of a guinea pig being approximately 350 g). Thus, FXIa showed an antitussive efficacy on both the laryngeal trachea and the tracheal bifurcation in a relatively extremely small amount, that is, from several ten-thousandth to ten-millionth of codeine.

BEST MODE FOR CARRYING OUT THE INVENTION

Depending on the duration, cough is generally classified into acute cough with duration of 3 weeks or less, prolonged cough with duration of 3 weeks or more and less than 8 weeks (also called as "subacute cough") and chronic cough with duration of 8 weeks or more. Cough is also broadly classified into productive cough and nonproductive cough, depending on its symptom. Productive cough means wet cough involving sputum or hemoptysis, and nonproductive cough means dry cough not involving them. "Cough" as used herein may include both of the above-described coughs as well as diseases involving the coughs.

As used herein, "chronic cough", referred to as intractable cough, means a disease involving cough with duration of 8 weeks or more without showing significant physical observations such as an abnormal chest roentgenogram, stridor, and the like. The specific examples of chronic cough include cough by Sino-Bronchial Syndrome (hereinafter also referred to as "SBS"), cough by postnasal discharge, cough by chronic bronchitis, cough by localized bronchiectasis, cough associated with bronchorrhea by bronchial asthma, cough by nonasthmatic eosinophilic bronchitis, cough by lung cancer (e.g. alveolar epithelial carcinoma), cough by bronchoesophageal fistula, cough by bronchial biliary fistula, Atopic Cough (hereinafter also referred to as "AC"), cough by Cough Variant Asthma (hereinafter also referred to as "CVA"), cough by oral administration of an ACE inhibitor, cough by gastroesophageal reflux, cough by pharynx allergia, cough by interstitial pneumonia, cough by lung fibrosis, psychosomatic cough, cough by bronchial tuberculosis, cough after acute upper respiratory tract infection (cold syndrome), and the like.

As used herein, "acute cough" is cough with duration of 3 weeks or less after onset of symptoms, including a case where abnormality is found in chest radiography or auscultatory observation. The cause of acute cough includes common cold, influenza, acute bronchitis, acute nose/paranasal sinus disease, acute exacerbation of a chronic respiratory tract disease, and the like.

As used herein, "prolonged cough" is cough with duration of 3 weeks or more and less than 8 weeks which is caused by the similar causes to chronic cough.

As used herein, "disease involving cough" includes a variety of respiratory diseases such as common cold, acute bronchitis, chronic bronchitis, bronchiectasis, pneumonia, phthisis pulmonum, silicosis and silicotuberculosis, lung cancer, upper respiratory tract inflammation (pharyngitis, laryngitis, nasal catarrh), asthmatic bronchitis, bronchial asthma, infantile asthma, (chronic) pneumonectasia, coniosis, lung fibrosis, silicosis, pulmonary suppuration, pleurisy, tonsillitis, cough hives, pertussis, as well as cough associated with bronchography, bronchoscopy, and the like.

As used herein, chronic cough is also broadly classified into productive cough and nonproductive cough but is not necessarily classified as shown below since it may sometimes involve both productive cough and nonproductive cough. Chronic cough involving productive cough includes cough by Sino-Bronchial Syndrome, cough by postnasal discharge, cough by chronic bronchitis, cough by localized bronchiectasis, cough associated with bronchorrhea by bronchial asthma, cough by nonasthmatic eosinophilic bronchitis, cough by lung cancer (e.g. alveolar cell carcinoma), cough by bronchoesophageal fistula, cough by bronchial biliary fistula, and the like. Chronic cough involving nonproductive cough includes Atopic Cough, cough by Cough Variant Asthma, cough by oral administration of an ACE inhibitor, cough by gastroesophageal reflux, cough by pharynx allergia, cough by interstitial pneumonia, cough by lung fibrosis, psychosomatic cough, cough by bronchial tuberculosis, cough after acute upper respiratory tract inflammation, and the like.

As used herein, "prevention" means keeping cough at its slightest level which may be relieved in a short period of time in case of its manifestation. "Treatment" means a decrease in the duration and the frequency of cough and elimination of cough. "Symptom amelioration" means prevention or alleviation and palliation of the above-described cough symptoms.

As used herein, "activated Factor XI" ("FXIa") includes both blood-borne FXIa (hereinafter also referred to as "nFXIa") and recombinant FXIa produced by a genetic recombination technique (hereinafter also referred to as "rFXIa"). FXIa may have an amino acid sequence of FXIa with one or several amino acids therein being deleted, substituted or added as long as it has the enzymatic activity of FXIa or may be a minimum unit having said enzymatic activity (hereinafter, such modified FXIa is also referred to as "mFXIa"). In this regard, "one or several amino acids" refers to 1, 2, 3, 4, or 5 amino acids or thereabout. Therefore, FXIa as used herein may encompass "nFXIa", "rFXIa" and "mFXIa".

Purification of "nFXIa" may be accomplished by suitably combining the methods commonly used in the field of protein chemistry such as centrifugation, salting-out, ultrafiltration, isoelectric point precipitation, electrophoresis, ion-exchanger chromatography, gel filtration chromatography, affinity chromatography, hydrophobic chromatography, hydroxyapatite chromatography, and the like. By way of an example, the purification may be accomplished by purifying FXI using anti-FXI monoclonal antibody immobilized on an affinity chromatography as described in the literature and then activating FXI to FXIa with activated Factor XII or thrombin (Characterization of Novel Forms of Coagulation Factor XIa: independence of factor XIa subunits in factor IX activated: J. Biol. Chem.: Smith S B, Verhamme I M, Sun M F, Bock P E, Gailani D.: 2008: 283: p 6696-6705).

Detection of an FXIa protein may be performed by a method based on a molecular size such as SDS-PAGE, gel filtration, or by a method based on an antigen-antibody reaction such as ELISA, Western blotting, dot blot, and the like. These processes are all ones commonly used for detecting foreign proteins and may suitably be selected depending on the purpose. An amount of the produced FXIa protein may be measured with a reagent for measurement of proteins such as BCA Protein Assay Reagent Kit (Pierce Biotechnology Inc.) and Protein Assay Kit (Bio-RAD Inc.).

An antibody to be used in these processes may be either a polyclonal antibody or a monoclonal antibody. In the case of a monoclonal antibody, it may be obtained by harvesting antibody-producing cells such as splenocytes, lymphocytes, and the like from an immunized animal, fusing the cells with myeloma cell lines according to Milstein et al. (Method Enzymol., 73, 3-46, 1981) to prepare a hybridoma producing an antibody to a specific antigen. An antibody binding to a specific antigen may also be produced by a procedure for producing antibodies utilizing a phage display technique (Phage Display of Peptides and Protein: A Laboratory Manual Edited by Brian K. Kay et al., Antibody Engineering: A PRACTICAL APPROACH Edited by J. McCAFFERTY et al., Antibody Engineering second edition edited by Carl A. K. BORREBEACK). For ELISA or Western blotting as described above, the obtained antibodies may be labeled by a method such as fluorescent labeling, RI and biotinylation. Kits for labeling antibodies, as commercially available, may be utilized.

rFXIa may be obtained in accordance with the method described in the literature (Expression of human Factor XI characterization of the defect in factor XI type III deficiency: Blood: Meijers J C, Davie E W, Chung D W: 1992: 15: p 1435-1440). More particularly, a gene encoding rFXIa may be amplified in a PCR reaction using PCR primers designed for the gene sequence, with a commercially available cDNA library for use as a template. The obtained PCR product may be incorporated into a plasmid vector and the vector introduced into *Escherichia coli*. A clone having cDNA encoding the desired protein may be selected from the colonies of *Escherichia coli*. Primers for PCR are readily available by entrusting DNA synthesis contractors such as QIAGEN. The KOZAK sequence (Kozak M., J. Mol. Biol., 196, 947, 1987) and a suitable restriction enzyme cleavage sequence may preferably be added to the 5' end of the primers. The PCR reaction may be performed using the commercially available Advantage HF-2 PCR kit (BD Bioscience Inc.) in accordance with the attached protocol. After cloning with a TA cloning kit (Invitrogen Inc.), and the like, a nucleotide sequence of the DNA fragment obtained by the PCR may be determined by a DNA sequencer such as CEQ2000XL DNA Analysis System (Beckman Inc.).

When a point mutation is to be introduced into the thus obtained rFXIa gene, a site directed mutagenesis method may generally be used. In practice, it may be performed by using a commercially available kit, to which the technology is applied, such as Site-Direction Mutagenesis System by Takara Inc. (Mutan-Super Express Km, Mutan-Express Km, Mutan-K, etc.), QuickChange Multi Site-Direction Mutagenesis kit or QuickChange XL Multi Site-Direction Mutagenesis kit by Stratagene Inc. and GeneTailor Site-Directed Mutagenesis System by Invitrogen Inc., and the like, in accordance with the attached protocols.

A recombinant FXIa (rFXIa protein) may be expressed by incorporating the rFXIa gene into a suitable expression vector and transforming a host with said expression vector. As a host, a bacterium, a yeast, an animal cell, a plant cell, an insect cell, and the like, as commonly used for expressing foreign proteins, may be used. Any host may be used as long as the expression product shows the enzymatic activity of FXIa. For purifying these proteins from the cells producing the rFXIa protein, the above purification method used in the field of protein chemistry may be used. Alternatively, the above modifications may also be performed by a chemical method.

The thus obtained FXIa may be diluted with saline, a buffer solution, and the like for a formulation to prepare a pharmaceutical composition. pH of the formulation may preferably be in a range of from mildly acidic to neutral so as to be close to pH of the body fluid. The lower limit of the pH is preferably from 5.0 to 6.4 and the upper limit of the pH is preferably from 6.4 to 8.0. The preparation may also be provided in such a form that allows for storage in a long period of time such as a lyophilized form. For this purpose, it may be used after being dissolved in water, saline, buffer solution, and the like at a desired concentration. The pharmaceutical composition of the present invention may comprise a pharmaceutically acceptable excipient commonly used for a medicament (e.g. a carrier, a vehicle and a diluent), a stabilizer or a pharmaceutically necessary component. A stabilizer includes a monosaccharide such as glucose, a disaccharide such as saccharose, maltose, a sugar alcohol such as mannitol, sorbitol, a neutral salt such as sodium chloride, an amino acid such as glycine, a nonionic surfactant such as polyethylene glycol, polyoxyethylene-polyoxypropylene copolymer (Pluronic), polyoxyethylene sorbitan fatty acid ester (Tween), human albumin, and the like, and may preferably be added at about 1-10 w/v %.

The pharmaceutical composition of the present invention may be administered by oral administration, intravenous injection, intramuscular injection, subcutaneous injection, local administration, transrectal administration, transdermal administration, nasal administration, intraperitoneal administration, pulmonic administration, and the like at an effective dose via a single dose or divided doses. The dose may vary depending on symptom, age, body weight, and the like, and preferably be 4.3 ng/kg or more, more preferably 43 ng/kg or more, even more preferably 429 ng/kg or more.

The pharmaceutical composition for oral administration may be in the form of a tablet, a capsule, powder or liquid. The tablet may comprise a solid carrier such as gelatin or an adjuvant. The liquid pharmaceutical composition may usually be prepared with a liquid carrier such as water, animal oil, plant oil, mineral oil, or synthetic oil. It may contain saline, glucose or other saccharide solution, or glycol such as ethylene glycol, propylene glycol, or polyethylene glycol.

In the case of an intravenous, cutaneous or subcutaneous injection, or an injection into a site of pain, the active component preferably does not comprise a pyrogenic factor and the composition may preferably be in a parenterally acceptable form of aqueous solution having proper pH, isotonicity and stability. A skilled person can prepare an appropriate solution, for example, by using an isotonic medium such as a sodium chloride solution, a Ringer's solution, a lactated Ringer's solution, and the like. The composition may include a preservative, a stabilizer, a buffer solution, an antioxidant, and/or other excipients as necessary.

The present invention also relates to a method of prevention, treatment and/or symptom amelioration of cough in a mammal, comprising administering to the mammal an effective amount of a full length amino acid sequence constituting activated Factor XI (hereinafter also referred to as "FXIa"), the amino acid sequence with one or several amino acids therein being deleted, substituted or added, or a partial sequence of either of the above amino acid sequences, or an amino acid sequence comprising as a part any of the above amino acid sequences.

The present invention is explained in more detail by means of the following example but should not be construed to be limited thereto.

Example 1

The guinea pig antitussive model was used according to Takahama et al. (Differential effect of codeine on coughs caused by a mechanical stimulation of two different sites in the airway of guinea pigs: Eur. J. Phamacol.: Takahama K. et al., 1997: 329: p 93-97). Male Hartley guinea pigs of 300-450 g were fixed under light anesthesia in the dorsal position, their trachea was exposed, and a small hole (0.5 mm×0.5 mm) was created at the position of 3.5 cm from the inferior border of the cricoid cartilage. A cough reflex was evoked by stimulating the respiratory tract mucosa around the laryngeal trachea and around the tracheal bifurcation with rabbit whisker. A pneumogram was recorded on a polygraph (RM-6100, NIHON KOHDEN CORPORATION) through a pneumotachograph (MEP-1100, NIHON KOHDEN CORPORATION) connected with a pneumograph placed on the abdomen. Stimulation was given at the tracheal bifurcation 25 minutes and 10 minutes before, and 5 minutes, 20 minutes, 35 minutes and 50 minutes after, the administration of the medicament, and was given at the laryngeal trachea 5 minutes after the respective stimulations of the tracheal bifurcation. The samples to be assessed were dialyzed against Dulbecco PBS (hereinafter referred to as "D-PBS") and 29 µL/kg was administrated from the brachial veins in principle at a concentration of 1.5 AU (absorbance unit) as an absorbance at 280 nm. The antitussive activity was assessed with the number of individuals where at least once a cough reflex in response to the stimulation at the tracheal bifurcation did not occur at all during assessment after administration of the medicament (effective number=the number of animals where a cough reflex did not occur/a total number of the assessed animals).

Twenty nine µL/kg of Factor XI (FXI), activated Factor XI (FXIa) and plasma kallikrein at 0.15-15 µg/mL was administrated to the guinea pig to assess the antitussive activity (all purchased from Haematologic Technologies Inc.). As a result, as shown in Table 1, a potent antitussive activity was observed for FXIa in spite of at an extremely small amount. On the other hand, no antitussive activity was found for the precursor FXI, plasma kallikrein, and the buffer used for dilution (D-PBS+0.1% human serum albumin). This antitussive activity of FXIa was reproduced with samples of different lots.

TABLE 1

Results of assessment of antitussive activity of purified samples of candidate proteins

| | Effective number* | |
| --- | --- | --- |
| Name of samples | Tracheal bifurcation | Laryngeal trachea |
| FXIa (Lot.A): 0.15 µg/mL | 5/6 | 3/6 |
| FXIa (Lot.A): 15 µg/mL | 3/6 | 3/6 |
| FXIa (Lot.B): 0.15 µg/mL | 4/7 | 4/7 |
| FXI: 0.15 µg/mL | 0/3 | 0/3 |
| Plasma Kallikrein: 0.15 µg/mL | 0/3 | 0/3 |
| Dilution buffer: D-PBS/0.1% HSA** | 0/3 | 0/3 |

*: The number of individuals where at least once a cough reflex in response to the stimulation at the tracheal bifurcation or at the laryngeal trachea did not occur at all during assessment after administration of the medicament, among a total number of the assessed animals.
**: Human serum albumin

INDUSTRIAL APPLICABILITY

The agent for prevention, treatment and/or symptom amelioration of cough of the present invention has a potent antitussive efficacy. Therefore, these medicaments and their pharmaceutically acceptable acid addition salts are expected to be a medicament applicable to any diseases involving cough, such as a variety of respiratory diseases such as common cold, acute bronchitis, chronic bronchitis, bronchiectasis, pneumonia, phthisis pulmonum, silicosis and silicotuberculosis, lung cancer, upper respiratory tract inflammation (pharyngitis, laryngitis, nasal catarrh), asthmatic bronchitis, bronchial asthma, infantile asthma, (chronic) pneumonectasia, coniosis (pneumoconiosis), lung fibrosis, silicosis, pulmonary suppuration, pleurisy, tonsillitis, cough urticaria, pertussis, and the like, cough associated with bronchography, bronchoscopy, and the like.

The invention claimed is:

1. A method for treating a subject having a cough comprising administering a comprising containing isolated or purified activated Factor XI (Factor XIa);
   wherein said Factor XIa has the amino acid sequence that is identical to that of Factor XIa isolated from human blood, or an amino acid sequence that contains a deletion of, a substitution to, or an addition to 1, 2, 3, 4, or 5 amino acid residues of said Factor XIa amino acid sequence, and wherein said Factor XIa is in an amount sufficient to treat coughing in the subject in need thereof.

2. The method of claim 1, wherein said composition contains an amount of activated Factor XI sufficient to treat a cough in a human.

3. The method of claim 1, wherein said composition contains an amount of activated Factor XI sufficient to treat a cough caused by stimulation at the tracheal bifurcation.

4. The method of claim 1, wherein said composition contains an amount of activated Factor XI sufficient to treat a cough caused by stimulation at the laryngeal trachea.

5. The method of claim 1, wherein said composition contains activated Factor XI which has an amino acid sequence that is identical to that of native Factor XIa isolated from human blood.

6. The method of claim 1, wherein said composition comprises activated Factor XI which has an amino acid sequence that contains a deletion of, a substitution to, or an addition to 1, 2, 3, 4, or 5 amino acid residues of the Factor XIa amino acid sequence identical to that of native Factor XIa isolated from human blood.

7. The method of claim 1, wherein said composition contains Factor XIa at a concentration ranging from 0.15 to 15 µg/ml.

8. The method of claim 1, wherein said composition contains a dosage of Factor XIa ranging from 4.3 ng/kg to 429 ng/kg.

9. The method of claim 1, wherein said composition contains a saline solution or a buffer solution having a pH ranging from 5.0 to 8.0.

10. The method of claim 1, wherein said composition contains a stabilizer in an amount of 1 to 10% w/v.

11. The method of claim 1, wherein said composition contains an amount of activated Factor XIa sufficient to treat a cough caused by mechanical stimulation at the tracheal bifurcation.

12. The method of claim 1, wherein said composition contains an amount of activated Factor XIa sufficient to treat a cough caused by mechanical stimulation at the laryngeal trachea.

* * * * *

SEQUENCE LISTING

<160> NUMBER OF SEQ ID NOS: 5

<210> SEQ ID NO 1
<211> LENGTH: 625
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: mat_peptide
<222> LOCATION: (19)..(625)

<400> SEQUENCE: 1

```
Met Ile Phe Leu Tyr Gln Val Val His Phe Ile Leu Phe Thr Ser Val
            -15                 -10                  -5

Ser Gly Glu Cys Val Thr Gln Leu Leu Lys Asp Thr Cys Phe Glu Gly
     -1   1                   5                  10

Gly Asp Ile Thr Thr Val Phe Thr Pro Ser Ala Lys Tyr Cys Gln Val
 15                  20                  25                  30

Val Cys Thr Tyr His Pro Arg Cys Leu Leu Phe Thr Phe Thr Ala Glu
                 35                  40                  45

Ser Pro Ser Glu Asp Pro Thr Arg Trp Phe Thr Cys Val Leu Lys Asp
             50                  55                  60

Ser Val Thr Glu Thr Leu Pro Arg Val Asn Arg Thr Ala Ala Ile Ser
         65                  70                  75

Gly Tyr Ser Phe Lys Gln Cys Ser His Gln Ile Ser Ala Cys Asn Lys
     80                  85                  90

Asp Ile Tyr Val Asp Leu Asp Met Lys Gly Ile Asn Tyr Asn Ser Ser
 95                 100                 105                 110

Val Ala Lys Ser Ala Gln Glu Cys Gln Glu Arg Cys Thr Asp Asp Val
                115                 120                 125

His Cys His Phe Phe Thr Tyr Ala Thr Arg Gln Phe Pro Ser Leu Glu
            130                 135                 140

His Arg Asn Ile Cys Leu Leu Lys His Thr Gln Thr Gly Thr Pro Thr
            145                 150                 155

Arg Ile Thr Lys Leu Asp Lys Val Val Ser Gly Phe Ser Leu Lys Ser
        160                 165                 170

Cys Ala Leu Ser Asn Leu Ala Cys Ile Arg Asp Ile Phe Pro Asn Thr
175                 180                 185                 190

Val Phe Ala Asp Ser Asn Ile Asp Ser Val Met Ala Pro Asp Ala Phe
                195                 200                 205

Val Cys Gly Arg Ile Cys Thr His His Pro Gly Cys Leu Phe Phe Thr
            210                 215                 220

Phe Phe Ser Gln Glu Trp Pro Lys Glu Ser Gln Arg Asn Leu Cys Leu
            225                 230                 235

Leu Lys Thr Ser Glu Ser Gly Leu Pro Ser Thr Arg Ile Lys Lys Ser
        240                 245                 250

Lys Ala Leu Ser Gly Phe Ser Leu Gln Ser Cys Arg His Ser Ile Pro
255                 260                 265                 270

Val Phe Cys His Ser Ser Phe Tyr His Asp Thr Asp Phe Leu Gly Glu
                275                 280                 285

Glu Leu Asp Ile Val Ala Ala Lys Ser His Glu Ala Cys Gln Lys Leu
            290                 295                 300

Cys Thr Asn Ala Val Arg Cys Gln Phe Phe Thr Tyr Thr Pro Ala Gln
305                 310                 315
```

```
Ala Ser Cys Asn Glu Gly Lys Gly Lys Cys Tyr Leu Lys Leu Ser Ser
    320                 325                 330

Asn Gly Ser Pro Thr Lys Ile Leu His Gly Arg Gly Gly Ile Ser Gly
335                 340                 345                 350

Tyr Thr Leu Arg Leu Cys Lys Met Asp Asn Glu Cys Thr Thr Lys Ile
                355                 360                 365

Lys Pro Arg Ile Val Gly Gly Thr Ala Ser Val Arg Gly Glu Trp Pro
            370                 375                 380

Trp Gln Val Thr Leu His Thr Thr Ser Pro Thr Gln Arg His Leu Cys
        385                 390                 395

Gly Gly Ser Ile Ile Gly Asn Gln Trp Ile Leu Thr Ala Ala His Cys
    400                 405                 410

Phe Tyr Gly Val Glu Ser Pro Lys Ile Leu Arg Val Tyr Ser Gly Ile
415                 420                 425                 430

Leu Asn Gln Ser Glu Ile Lys Glu Asp Thr Ser Phe Phe Gly Val Gln
                435                 440                 445

Glu Ile Ile Ile His Asp Gln Tyr Lys Met Ala Glu Ser Gly Tyr Asp
            450                 455                 460

Ile Ala Leu Leu Lys Leu Glu Thr Val Asn Tyr Thr Asp Ser Gln
        465                 470                 475

Arg Pro Ile Cys Leu Pro Ser Lys Gly Asp Arg Asn Val Ile Tyr Thr
    480                 485                 490

Asp Cys Trp Val Thr Gly Trp Gly Tyr Arg Lys Leu Arg Asp Lys Ile
495                 500                 505                 510

Gln Asn Thr Leu Gln Lys Ala Lys Ile Pro Leu Val Thr Asn Glu Glu
                515                 520                 525

Cys Gln Lys Arg Tyr Arg Gly His Lys Ile Thr His Lys Met Ile Cys
            530                 535                 540

Ala Gly Tyr Arg Glu Gly Gly Lys Asp Ala Cys Lys Gly Asp Ser Gly
        545                 550                 555

Gly Pro Leu Ser Cys Lys His Asn Glu Val Trp His Leu Val Gly Ile
    560                 565                 570

Thr Ser Trp Gly Glu Gly Cys Ala Gln Arg Glu Arg Pro Gly Val Tyr
575                 580                 585                 590

Thr Asn Val Val Glu Tyr Val Asp Trp Ile Leu Glu Lys Thr Gln Ala
                595                 600                 605

Val

<210> SEQ ID NO 2
<211> LENGTH: 90
<212> TYPE: PRT
<213> ORGANISM: Homo sapiens

<400> SEQUENCE: 2

Glu Cys Val Thr Gln Leu Leu Lys Asp Thr Cys Phe Glu Gly Gly Asp
1               5                   10                  15

Ile Thr Thr Val Phe Thr Pro Ser Ala Lys Tyr Cys Gln Val Val Cys
            20                  25                  30

Thr Tyr His Pro Arg Cys Leu Leu Phe Thr Phe Thr Ala Glu Ser Pro
        35                  40                  45

Ser Glu Asp Pro Thr Arg Trp Phe Thr Cys Val Leu Lys Asp Ser Val
    50                  55                  60
```

-continued

Thr Glu Thr Leu Pro Arg Val Asn Arg Thr Ala Ala Ile Ser Gly Tyr
 65                  70                  75                  80

Ser Phe Lys Gln Cys Ser His Gln Ile Ser
                 85                  90

<210> SEQ ID NO 3
<211> LENGTH: 90
<212> TYPE: PRT
<213> ORGANISM: Homo sapiens

<400> SEQUENCE: 3

Ala Cys Asn Lys Asp Ile Tyr Val Asp Leu Asp Met Lys Gly Ile Asn
  1               5                  10                  15

Tyr Asn Ser Ser Val Ala Lys Ser Ala Gln Glu Cys Gln Glu Arg Cys
                 20                  25                  30

Thr Asp Val His Cys His Phe Thr Tyr Ala Thr Arg Gln Phe
             35                  40                  45

Pro Ser Leu Glu His Arg Asn Ile Cys Leu Leu Lys His Thr Gln Thr
         50                  55                  60

Gly Thr Pro Thr Arg Ile Thr Lys Leu Asp Lys Val Val Ser Gly Phe
 65                  70                  75                  80

Ser Leu Lys Ser Cys Ala Leu Ser Asn Leu
                 85                  90

<210> SEQ ID NO 4
<211> LENGTH: 91
<212> TYPE: PRT
<213> ORGANISM: Homo sapiens

<400> SEQUENCE: 4

Ala Cys Ile Arg Asp Ile Phe Pro Asn Thr Val Phe Ala Asp Ser Asn
  1               5                  10                  15

Ile Asp Ser Val Met Ala Pro Asp Ala Phe Val Cys Gly Arg Ile Cys
                 20                  25                  30

Thr His His Pro Gly Cys Leu Phe Phe Thr Phe Phe Ser Gln Glu Trp
             35                  40                  45

Pro Lys Glu Ser Gln Arg Asn Leu Cys Leu Leu Lys Thr Ser Glu Ser
         50                  55                  60

Gly Leu Pro Ser Thr Arg Ile Lys Lys Ser Lys Ala Leu Ser Gly Phe
 65                  70                  75                  80

Ser Leu Gln Ser Cys Arg His Ser Ile Pro Val
                 85                  90

<210> SEQ ID NO 5
<211> LENGTH: 90
<212> TYPE: PRT
<213> ORGANISM: Homo sapiens

<400> SEQUENCE: 5

Phe Cys His Ser Ser Phe Tyr His Asp Thr Asp Phe Leu Gly Glu Glu
  1               5                  10                  15

Leu Asp Ile Val Ala Ala Lys Ser His Glu Ala Cys Gln Lys Leu Cys
                 20                  25                  30

Thr Asn Ala Val Arg Cys Gln Phe Phe Thr Tyr Thr Pro Ala Gln Ala
             35                  40                  45

Ser Cys Asn Glu Gly Lys Gly Lys Cys Tyr Leu Lys Leu Ser Ser Asn
         50                  55                  60

Gly Ser Pro Thr Lys Ile Leu His Gly Arg Gly Gly Ile Ser Gly Tyr
 65                  70                  75                  80

```
Thr Leu Arg Leu Cys Lys Met Asp Asn Glu
                85                  90
```